(12) United States Patent
Tanaka (10) Patent No.: US 9,328,365 B2
(45) Date of Patent: May 3, 2016

(54) PROCESS FOR PRODUCING SACCHARIFIED SOLUTION

(71) Applicant: HONDA MOTOR CO., LTD., Tokyo (JP)

(72) Inventor: Hiroyuki Tanaka, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 67 days.

(21) Appl. No.: 13/903,717

(22) Filed: May 28, 2013

(65) Prior Publication Data

US 2014/0045224 A1  Feb. 13, 2014

(30) Foreign Application Priority Data

Aug. 9, 2012 (JP) ................. 2012-177385

(51) Int. Cl.
C12P 19/14 (2006.01)
C12P 19/02 (2006.01)

(52) U.S. Cl.
CPC *C12P 19/14* (2013.01); *C12P 19/02* (2013.01)

(58) Field of Classification Search
None
See application file for complete search history.

(56) References Cited

U.S. PATENT DOCUMENTS

| | | | |
|---|---|---|---|
| 7,932,063 B2 * | 4/2011 | Dunson et al. | 435/99 |
| 8,563,282 B2 * | 10/2013 | Galvez et al. | 435/161 |
| 2009/0053777 A1 * | 2/2009 | Hennessey et al. | 435/101 |

FOREIGN PATENT DOCUMENTS

| | | |
|---|---|---|
| JP | 01-234656 | 9/1989 |
| JP | 2009-189250 | 8/2009 |
| JP | 2009-240168 A | 10/2009 |
| JP | 2011-098262 | 5/2011 |
| JP | 2011-223975 | 11/2011 |
| WO | 2011/162009 | 12/2011 |

OTHER PUBLICATIONS

Taherzadeh, Mohammad; et al; "Pretreatment of Lignocellulosic Wastes to Improve Ethanol and Biogas Production: A Review" International Journal of Molecular Sciences, 9, 1621-1651, 2008.*
Mosier, Nathan; et al; "Features of promising technologies for pretreatment of lignocellulosic biomass" Bioresource Technology, 96, 673-686, 2005.*
Sun, Ye; et al; "Hydrolysis of lignocellulosic materials for ethanol production: a review" Bioresource Technology, 83, 1-11, 2002.*
Japanese Office Action date Jan. 12, 2016, 6 pages.

* cited by examiner

*Primary Examiner* — Renee Claytor
*Assistant Examiner* — David Berke-Schlessel
(74) *Attorney, Agent, or Firm* — Rankin, Hill & Clark LLP (57) ABSTRACT

A process for producing a saccharified solution in an improved yield when filtering the mixture obtained by saccharifying lignocellulosic biomass is provided. A mixture containing a saccharified solution and an undecomposed biomass residue by treating a substrate biomass using a saccharification enzyme is obtained. The mixture is filtered to obtain the saccharified solution as a filtrate. Before filtering the mixture, 95% by mass or more of the particles, based on the total amount of particles contained in a centrifuged supernatant of the mixture, is adjusted to have a particle size ranging from 1 to 30 μm.

7 Claims, 6 Drawing Sheets

PROCESS FOR PRODUCING SACCHARIFIED SOLUTION

BACKGROUND OF THE INVENTION

Detailed Description of the Invention

1. Field of the Invention

The present invention relates to a process for producing a saccharified solution.

2. Description of the Related Art

Up to date, a process for producing bioethanol having a substrate of lignocellulosic biomass is known. According to the process for producing bioethanol described above, the lignocellulosic biomass is saccharified using a saccharification enzyme to obtain a saccharified solution, which is then fermented using a fermentation microorganism, yeast, or the like, whereby a fermented solution containing ethanol is obtained. Subsequently, the fermented solution can be condensed using a technique such as distillation, or the like, to obtain bioethanol (see, for example, Japanese Patent Laid-Open No. 2009-240168).

When the lignocellulosic biomass is saccharified using a saccharification enzyme, the cellulose or hemicellulose contained in the lignocellulosic biomass is first hydrolyzed by the saccharification enzyme, thereby producing a saccharified solution. At this step, lignin contained in the lignocellulosic biomass is not hydrolyzed and remains undecomposed. A part of the cellulose or hemicellulose contained in the lignocellulosic biomass also remains undecomposed. As a result, a mixture of the undecomposed biomass residues, such as lignin, cellulose and hemicellulose, and the saccharified solution is obtained.

Thus, it is desired to obtain the saccharified solution by the removal of the biomass residues by subjecting the mixture to solid-liquid separation. Examples of the unit which removes the biomass residues from the mixture by the solid-liquid separation include filtration units such as filter press.

However, when the mixture obtained by saccharifying lignocellulosic biomass using a saccharification enzyme is filtered using the filtration units described above, the saccharified solution is not produced in a sufficient yield, hence inconvenient.

SUMMARY OF THE INVENTION

The present invention has an object to provide a process for producing a saccharified solution which overcomes the above inconvenience and is capable of improving the yield of the saccharified solution when filtering the mixture using the above filtration unit.

To achieve such an object, the process for producing a saccharified solution of the present invention comprises: a step of obtaining a mixture containing a saccharified solution and an undecomposed biomass residue by treating a substrate biomass using a saccharification enzyme; and a step of obtaining the saccharified solution as a filtrate by filtering the mixture using a filtration device; and the process, before filtering the mixture using the filtration unit, further comprises a step of adjusting the mixture so that 95% by mass or more of the particles, based on the total amount of particles contained in the centrifuged supernatant obtained after the mixture is centrifuged, has a particle size ranging from 1 to 30 µm.

According to the process for producing a saccharified solution of the present invention, biomass to be a substrate is first treated using a saccharification enzyme. In this way, the components such as cellulose and hemicellulose contained in the biomass are hydrolyzed by the saccharification enzyme and converted into saccharides, whereby a saccharified solution is produced. On the other hand, the biomass is not entirely saccharified, but the components not saccharified by nature such as lignin, and unsaccharified parts of the saccharifiable components such as cellulose and hemicellulose, remain undecomposed.

Accordingly, the treatment using the saccharification enzyme provides a mixture containing the undecomposed biomass residues and the saccharified solution. The unsaccharified parts of the saccharifiable components such as cellulose and hemicellulose, and lignin contained in the biomass are microparticulated as a result of the hydrolysis, and the particles have an extremely broad particle size distribution.

In the filtration unit described above, a cake on a filter fabric is clogged up with the microparticles in the undecomposed biomass residues. The case is composed of undecomposed biomass residues. For this reason, it is difficult to filter the mixture without further treatment and the saccharified solution is hardly obtained in a sufficient yield even the filtration is carried out over an extended period of time.

Thus, in the process for producing a saccharified solution of the present invention, 95% by mass or more of the particles, based on the total amount of particles contained in a centrifuged supernatant obtained after the mixture is centrifuged, is adjusted to have a particle size ranging from 1 to 30 µm before the mixture is filtered using the above filtration unit. The adjustment to the particles can be carried out by flocculating microparticles having a particle size of less than 1 µm and contained in the centrifuged supernatant with each other.

According to the process for producing a saccharified solution of the present invention, the mixture can be easily solid-liquid separated into the undecomposed biomass residue in the form of solid and the saccharified solution in the form of filtrate by the above procedure, thereby improving the yield of the saccharified solution. When the particle having a particle size ranging from 1 to 30 µm is less than 95% by mass based on the total amount of particles contained in the centrifuged supernatant, microparticles are present in a relatively large proportion, causing clogging in the filtration unit and failing to sufficiently yield the saccharified solution.

When the particles have a particle size of less than 1 µm, clogging is caused in the filtration unit. The particles are flocculated microparticles contained in the supernatant obtained by centrifuging the mixture, and thus the particles having a particle size exceeding 30 µm are not substantially present.

In the process for producing a saccharified solution of the present invention, the particle adjustment, for example, can be carried out so that the $\zeta$ potential of the particle surface ranges from −3 to +3 mV. Thus, the particles having a particle size of less than 1 µm among the particles contained in the centrifuged supernatant are flocculated with each other and form particles having a particle size ranging from 1 to 30 µm. Consequently, 95% by mass or more of the particles based on the total amount of the particles contained in the centrifuged supernatant can be adjusted to have a particle size ranging from 1 to 30 µm.

The $\zeta$ potential of the particle surface can be, for example, carried out by adjusting pH of the mixture. The pH adjustment may be carried out by adding acid to the mixture, or by adjusting a temperature of the mixture to 40 to 55° C. In this instance, the pH of the mixture, at a temperature of the mixture of less than 40° C., may not be adjusted so that the $\zeta$ potential of the particle surface ranges from −3 to +3 mV. On the other hand, when a temperature of the mixture exceeds 55° C., the saccharification enzyme is deactivated, making it difficult to collect the saccharification enzyme from the mixture for reuse.

In the process for producing a saccharified solution of the present invention, the particle adjustment may be carried out, for example, by adding a precipitation agent to the mixture to allow the particles having a particle size of less than 1 μm to precipitate.

In the process for producing a saccharified solution of the present invention, the filtration is preferably carried out using, as a filtration unit, a filter press having a structure consisting of a plurality of vertical filter plates arranged parallelly, a filter chamber formed between a pair of adjacent filter plates and filter cloths lined along the internal configuration of the filter chambers, by feeding the mixture into the filter chamber under applied pressure, allowing a cake to form on the filter cloths, and then pressing the plurality of filter plates arranged parallelly in a direction in which one thereof overlaps another, whereby the mixture in the filter chamber is clamped between the filter cloths.

When the mixture is filtered using the filter press, the mixture is first fed into the filter chambers under applied pressure. As a result, the cake is formed on the filter cloths. The cake is composed of the undecomposed biomass residues.

At this step, the mixture is adjusted so as to contain 95% by mass or more of the particles, based on the total amount of the particles contained in the centrifuged supernatant, having a particle size ranging from 1 to 30 μm, thereby forming on the filter cloths the cake to be a preferable filter medium for the filtration of the mixture.

Consequently, in the filter press, the mixture is subsequently clamped between the filter cloths after the formation of the cake, thereby filtering the mixture using the cake as the filter medium. As a result, the filter press is capable of providing a clear saccharified solution as a filtrate substantially free of the undecomposed biomass residue particles.

The process for producing a saccharified solution of the present invention can be preferably used when the biomass is lignocellulosic biomass.

DETAILED DESCRIPTION OF THE PREFERRED EMBODIMENTS

Hereinafter, the embodiment of the present invention is further described in detail with reference to the drawings attached herewith.

Figure 1:
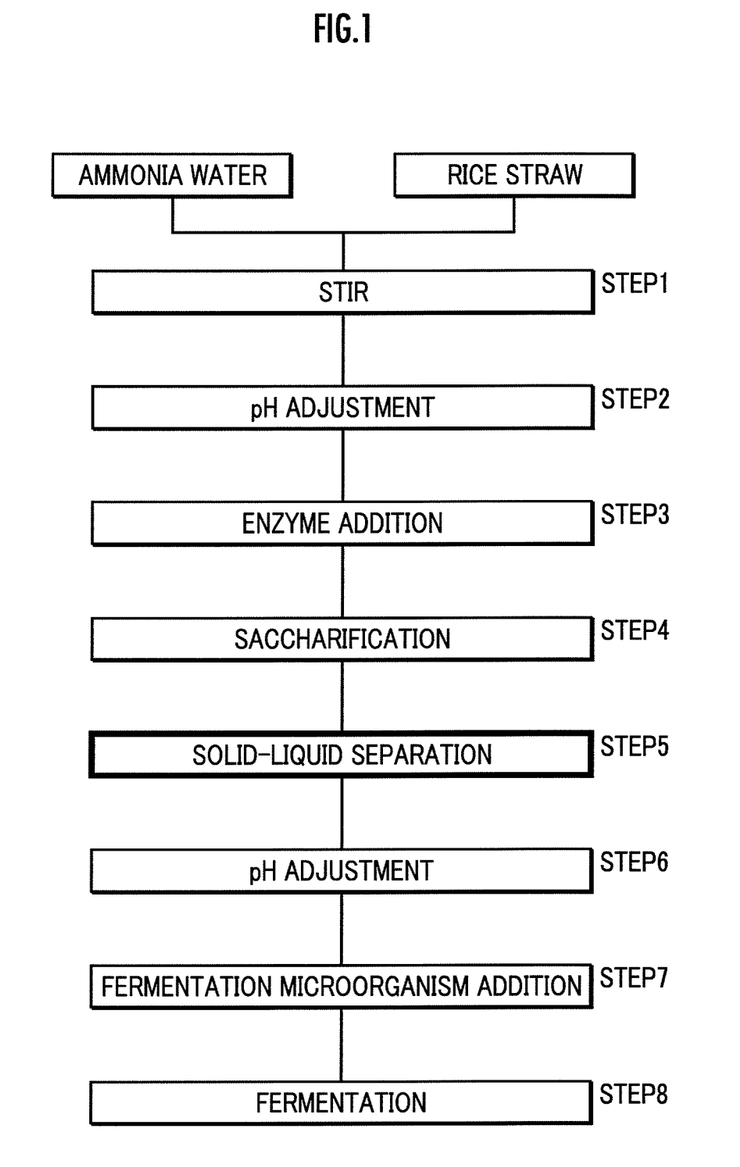
FIG. 1 is a flow chart illustrating the process for producing a saccharified solution of the present invention.

As shown in FIG. 1, rice straw is used as a lignocellulosic biomass substrate in the process for producing a saccharified solution of the present embodiment. In the process for producing a saccharified solution of the present embodiment, ammonia water is first added to the coarsely crushed rice straw and stirred (STEP 1) to obtain a substrate mixture containing the rice straw and ammonia.

The ammonia water at this step is contained in a concentration range of 20 to 30% by mass/volume, for example, 25% by mass/volume, and is mixed in a mass ratio to the rice straw so that rice straw:ammonia water=1:0.7 to 1:1.3. The obtained substrate mixture is kept at a temperature ranging from 25 to 100° C., for example, at a temperature of 80° C., for time ranging from 2 to 200 hours, for example, for 3 hours.

Consequently, lignin is dissociated from the rice straw substrate, or an ammonia-containing pretreated product for saccharification of the swollen rice straw is obtained. The ammonia-containing pretreated product for saccharification has pH ranging from 13 to 14 as a result of the ammonia water treatment.

In the present specification, the dissociation refers to the cleavage of at least a part of the bonds at the binding site of lignin binding to cellulose or hemicellulose. The swelling refers to the expansion caused by the gap generated in the cellulose or hemicellulose composing the crystalline cellulose or caused by the gap generated inside the cellulose fiber, due to the liquid permeation.

Ammonia is then separated by the dissipation from the ammonia-containing pretreated product for saccharification to obtain an ammonia-separated pretreated product for saccharification.

Subsequently, the pH of the ammonia-separated pretreated product for saccharification is adjusted (STEP 2). The pH of the ammonia-separated pretreated product for saccharification is adjusted to the pH range from 3 to 7 at which a saccharification enzyme can be active, for example, to pH 4.0. The above pH adjustment can be carried out by adding at least one acid from phosphoric acid, nitric acid and sulfuric acid, for example, a 5%-by-mass of dilute sulfuric acid, to the ammonia-separated pretreated product for saccharification.

A saccharification enzyme is then added to the ammonia-separated pretreated product for saccharification having the pH adjusted as described above to prepare a substrate/saccharification enzyme mixture (STEP 3). The saccharification enzyme is a saccharification enzyme produced by microorganisms and, for example, Acremonium cellulase (tradename, a product of Meiji Seika Pharma Co., Ltd.) or the like, can be used. The saccharification enzyme is added, based on the total amount of the substrate/saccharification enzyme mixture, in the range of 3.23 to 32.28% by mass, for example, 8% by mass. In this step, the substrate content in the substrate/saccharification enzyme mixture is 15 to 30% by mass, for example, 26% by mass.

Subsequently, the substrate/saccharification enzyme mixture is saccharified (STEP 4). The saccharification treatment is carried out by keeping the substrate/saccharification enzyme mixture at a temperature ranging from 30 to 60° C., for example, at a temperature of 30° C., for 50 to 150 hours, for example, for 144 hours. In this step, when the mixture is saccharified at a temperature ranging from, for example, 40 to 55° C. as to be described later, the mixture is maintained for 36 to 96 hours.

Owing to the saccharification treatment, the cellulose or hemicellulose contained in the rice straw is hydrolyzed by the action of the saccharification enzyme, whereby a saccharified solution is produced. On the other hand, the components not saccharified by nature such as lignin, and unsaccharified parts of the saccharifiable components such as cellulose and hemicellulose, contained in the rice straw remain undecomposed. In this step, the unsaccharified parts of the saccharifiable components such as cellulose and hemicellulose are microparticulated as a result of the hydrolysis.

Thus, the mixture containing the undecomposed biomass residues composed of lignin and microparticulated cellulose, hemicellulose, and the like, and the saccharified solution containing saccharides such as glucose and xylose, is obtained.

The mixture is then subjected to the solid-liquid separation by filtration to remove the undecomposed biomass residues, whereby the saccharified solution is obtained (STEP 5). The saccharified solution is subsequently adjusted so as to have a pH range in which a fermentation microorganism, yeast, and the like, can be active (STEP 6), and a fermentation microorganism, yeast, or the like, is then added thereto (STEP 7). The mixture is kept at a predetermined temperature range for a predetermined time range to carry out the fermentation treatment using the above fermentation microorganism, yeast, or the like (STEP 8), whereby a bioethanol-containing fermented solution can be obtained.

The mixture subjected to the solid-liquid separation in STEP 5 contains the undecomposed biomass residues as described above. The biomass residues are composed of lignin contained in the rice straw and the undecomposed components remained when the cellulose or hemicellulose described above is hydrolyzed by the action of the saccharification enzyme, and hence have an extremely broad particle size distribution from microparticles to coarse particles. For this reason, when the mixture is filtered without further treatment using a filtration unit such as a filter press, the saccharified solution cannot be obtained in a sufficient yield even the filtration is carried out at high press pressure and the filtration efficiency is also low even the filtration is carried out over an extended period of time.

Figure 2A:
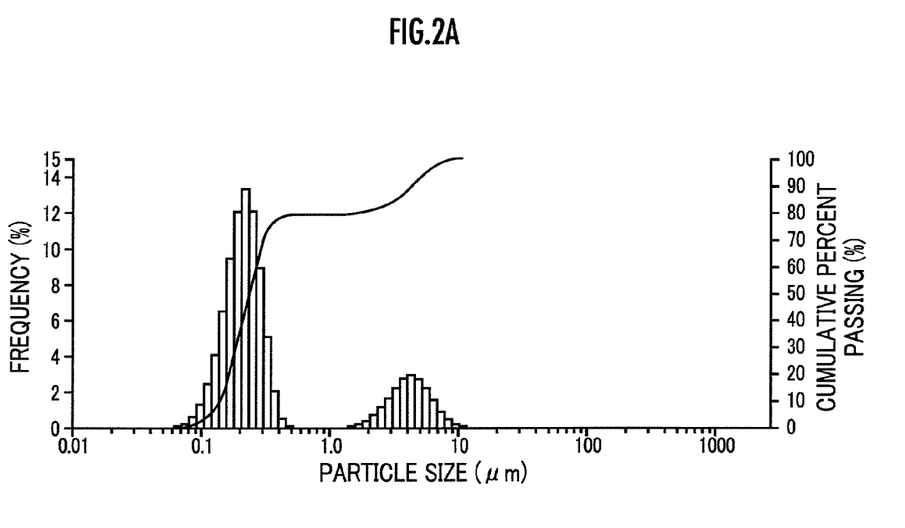
FIG. 2A is a graph showing the particle size distribution of the particles contained in the centrifuged supernatant obtained after the mixture obtained by the process for producing a saccharified solution of the present invention is centrifuged.

FIG. 2A shows the particle size distribution of the particles contained in the centrifuged supernatant produced after the mixture, obtained by saccharifying the substrate/saccharification enzyme mixture while kept at 30° C. for 144 hours, is centrifuged at 13000×g for 30 minutes.

FIG. 2A reveals that the particle size distribution of the particles contained in the supernatant has 2 peaks, one with an average particle size of 0.2 μm and the other with an average particle size of 5 μm. Accordingly, in the present embodiment, the particles forming the peak with an average particle size of 0.2 μm are coarsed and 95% by mass or more of the particles based on the total amount of the particles contained in the supernatant is adjusted to have a particle size ranging from 1 to 30 μm.

Figure 2B:
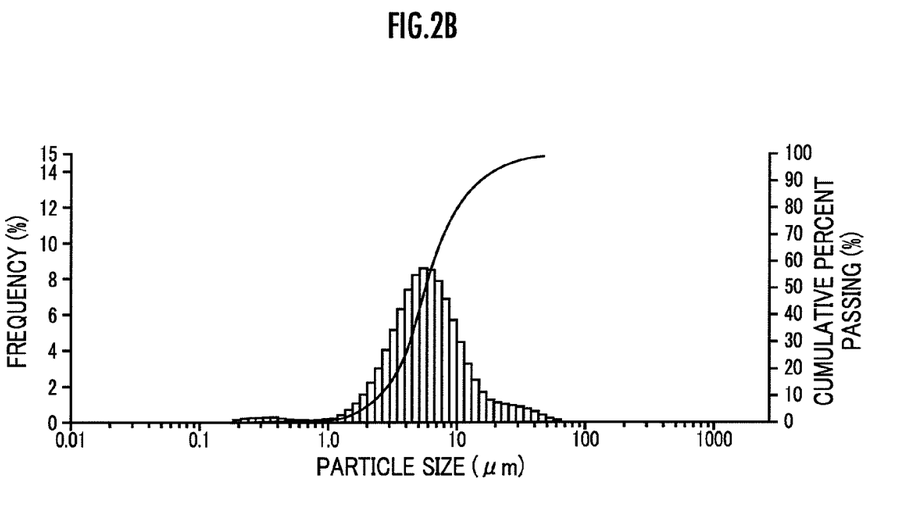
FIG. 2B is a graph showing the particle size distribution of the particles contained in the centrifuged supernatant after the particles forming the peak with an average particle size of 0.2 μm contained in the centrifuged supernatant are coarsed.
Figure 3:
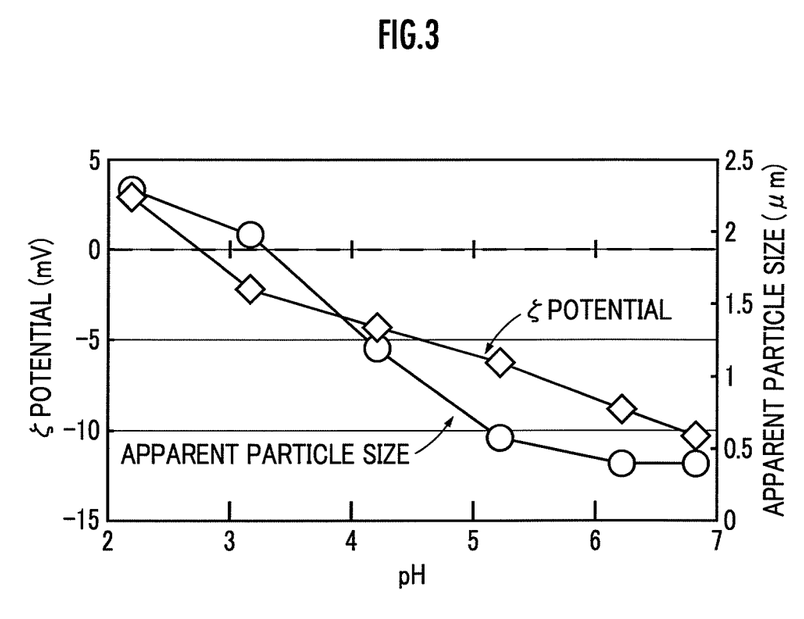
FIG. 3 is a graph showing the relation between the pH of the mixture obtained by the process for producing a saccharified solution of the present invention and the ζ potential and the apparent particle size of the particles contained in the centrifuged supernatant obtained after the mixture is centrifuged.

The particle size distribution described above can be adjusted, for example, by adjusting the pH of the mixture to a range of 2.0 to 3.5. As shown in FIG. 3, when the pH of the mixture is adjusted to the range described above, the ζ potential of the surface of particles contained in the supernatant can be ranged from −3 to +3 mV. As a result, the particles forming the peak with an average particle size of 0.2 μm can be caused to flocculate with each other and coarsed. Thus, as shown in FIG. 2B, 95% by mass or more of the particles based on the total amount of the particles contained in the supernatant can be adjusted to have a particle size ranging from 1 to 30 μm.

Subsequently, in the present embodiment, the mixture in which the particle size distribution of the particles contained in the supernatant is adjusted as described above is subjected to solid-liquid separation by filtration using a filtration unit to obtain the saccharified solution.

Figure 4A:
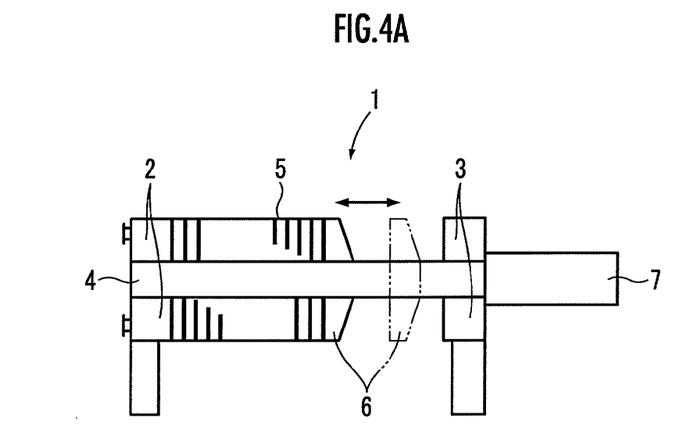
FIG. 4A is a plan view illustrating a structure example of the filter press.

A filter press 1 illustrated in FIG. 4, for example, can be used to be the above filtration unit. The filter press 1, as illustrated in FIG. 4A, is equipped with a plurality of vertical filter plates 5 arranged parallelly on a guide rail 4 suspended between a front frame 2 and a rear frame 3 and a pressing member 6 disposed on the rear frame 3 side of the filter plates 5. The filter plates 5 are movably supported along the guide rail 4, and the pressing member 6 operated by an oil hydraulic cylinder 7 presses the filter plates 5 in the direction of the front frame 2.

Figure 4B:
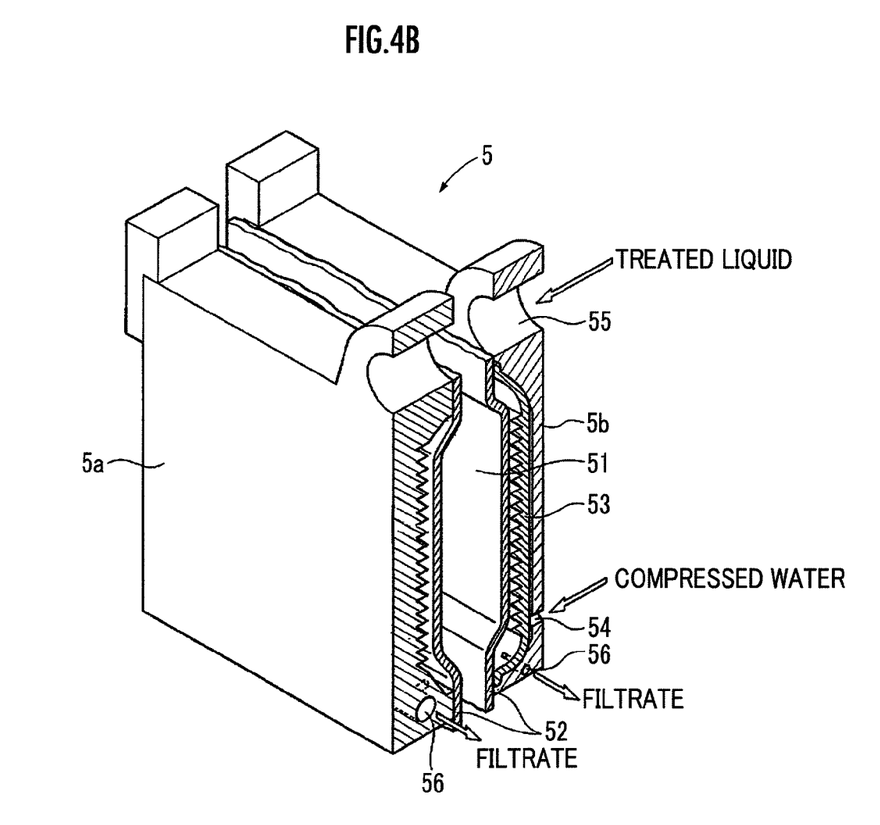
FIG. 4B is a partially cutout perspective view illustrating the filter plate composing the filter press.

The filter plates 5, as illustrated in FIG. 4B, are typically composed of a filter plate 5a and a diaphragm filter plate 5b positioned opposite to each other and forming a filter chamber 51 between a pair of adjacent filter plates 5a, 5b. The filter plates 5a, 5b have filter cloths 52 lined along the internal configuration thereof.

The diaphragm filter plate 5b has a diaphragm 53 positioned between the diaphragm filter plate 5b and the filter cloth 52, and the diaphragm 53 moves by compressed water injected from a compressed water injection tunnel 54 and typically turns to the filter plate 5a side.

The filter chamber 51 has a treated liquid supply path 55 arranged at the upper part thereof to supply a treated liquid to the filter chamber 51, and the filter chamber 51 has a filtrate drain path 56 arranged at the lower part thereof to discharge a filtrate. LASTA Filter (tradename, a product of ISHIGAKI COMPANY, LTD.), for example, can be used as the filter press composed of such a structure.

When the mixture is filtered using the filter press 1, the mixture is first fed under applied pressure into the filter chambers 51 from the treated liquid supply path 55 and a cake is formed on the filter cloths 52. The cake, together with the filter cloths 52, serves to be a filter medium when the mixture is filtered.

The cake can be formed on the filter cloths 52 so as to have a thickness ranging from 1 to 5 mm, for example, a thickness of 3 mm, by feeding the mixture into the filter chambers 51 for 10 minutes at a pressure of 0.1 MPa, for example. This procedure enables to provide, as a filtrate, a clear saccharified solution practically free of the undecomposed biomass residue particles in a sufficient yield.

It is technically difficult to provide the cake having a thickness of less than 1 mm. When the cake has a thickness exceeding 5 mm, the pressure for compressing to be described later must be high. However, a high pressure fails to provide the saccharified solution in a sufficient yield, and the energy required to perform the filtration also becomes enormous, increasing the production cost.

When the cake has been formed, the pressing member 6 is then operated by the oil hydraulic cylinder 7 to press the plurality of filter plates 5 arranged parallelly in a direction in which one overlaps another (in the direction of the front frame 2). At the same time, the diaphragm 53 is operated and typically turned to the filter plate 5a side to clamp the mixture in the filter chamber 51 between the filter cloths 52. The compressing is carried out at a pressure ranging from 1.0 to 3.0 MPa, for example, at a pressure of 1.5 MPa, for period of time ranging from 30 to 120 minutes, for example, for 90 minutes.

This procedure enables to provide a clear saccharified solution practically free of the undecomposed biomass residues in a high filtration yield.

Figure 5:
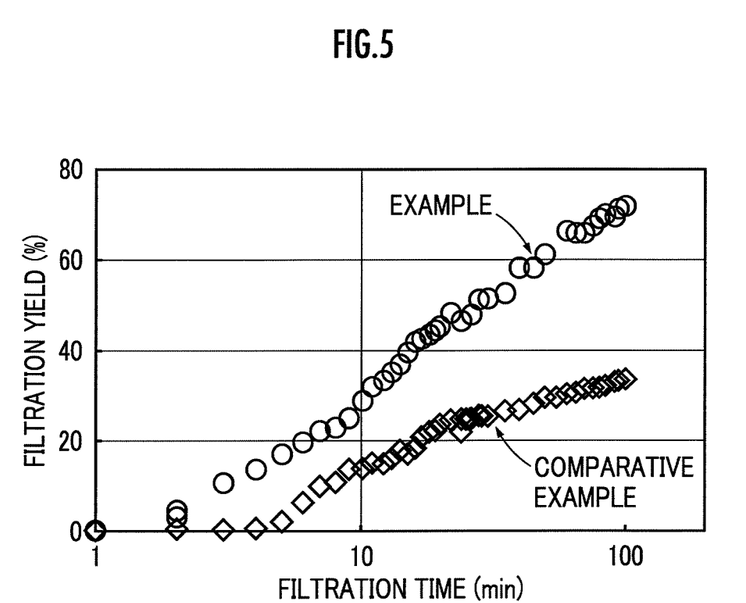
FIG. 5 is a graph showing the filtration yield by the process for producing a saccharified solution of the present invention.

Next, FIG. 5 shows the relation between the filtration time and the filtration yield when the mixture is adjusted to have the particle size distribution of the particles contained in the supernatant according to the production process of the present embodiment (Example) and otherwise. FIG. 5 reveals that the filtration yield after 100 minutes of filtration (the total of feeding time under applied pressure and compressing time) is less than 40% in a Comparative Example, whereas the yield is 70% or more in the Example. Thus, according to the production process of the present embodiment, it is evident that the yield of the saccharified solution can be improved.

Figure 6:
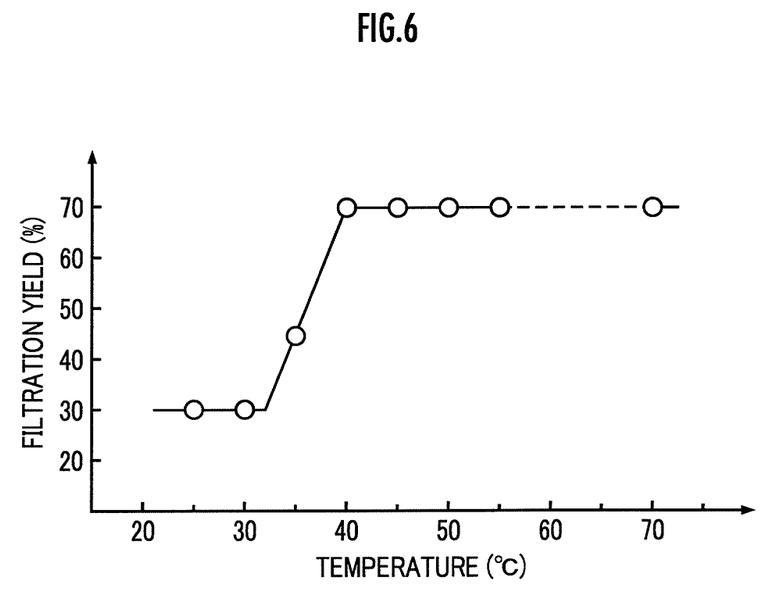
FIG. 6 is a graph showing the relation between the temperature of the mixture and the filtration yield in the process for producing a saccharified solution of the present invention.

The pH adjustment of the mixture, for example, may be carried out by adding acid, but may also be carried out by heating the mixture to a temperature ranging from 40 to 55° C. As shown in FIG. 6, when the mixture is heated to a temperature ranging from 40 to 55° C., it is apparent that the filtration yield abruptly increases in comparison with the case in which the temperature of the mixture is less than 30° C.

Instead of heating the mixture, the same particle size distribution as FIG. 2B can be attained when enzymatic saccharification is carried out at a temperature of 40 to 55° C. at the time of preparing the substrate/saccharification enzyme mixture by adding a saccharification enzyme to the ammonia-separated pretreated product for saccharification. Thus, the same effect can also be achieved in this case.

The heating may be carried out at a temperature of 55° C. or higher, for example, at a temperature of 60° C., but the typical saccharification enzyme is deactivated in such an instance, making it difficult to collect the saccharification enzyme for reuse. For this reason, when the heating is carried out at 55° C. or higher, it is preferable to use a heat resistant saccharification enzyme.

Alternatively, the mixture may be adjusted to have the particle size distribution of the particles contained in the supernatant by adding, instead of the pH adjustment described above, a precipitation agent thereto which precipitates particles forming the peak with an average particle size of 0.2 μm. However, it is required to select the precipitation agent which does not mix in the saccharified solution nor affect the fermentation of the saccharified solution, and alum, for example, can be used as such a precipitation agent.

What is claimed is:

1. A process for producing a saccharified solution, comprising:
    a step of treating a substrate biomass using a saccharification enzyme to obtain a mixture containing a saccharified solution and an undecomposed biomass residue;
    a step of adjusting 95% by mass or more of particles, based on a total amount of particles contained in a centrifuged supernatant obtained after the mixture is centrifuged, so as to have a particle size ranging from 1 to 30 μm, by flocculating microparticles having a particle size of less than 1 μm and contained in the centrifuged supernatant with each other; and
    a step of filtering the mixture using a filtration unit to obtain the saccharified solution as a filtrate.

2. The process for producing a saccharified solution according to claim 1, wherein the particle adjustment is carried out so that a potential of the particle surface ranges from −3 to +3 mV by adjusting a pH of the mixture in a range from 2.0 to 3.5.

3. The process for producing a saccharified solution according to claim 2, wherein the pH adjustment of the mixture is carried out while adjusting a temperature of the mixture in a range of 40 to 55° C.

4. The process for producing a saccharified solution according to claim 1, wherein the particle adjustment is carried out by adding a precipitation agent which does not mix in the saccharified solution nor affect a fermentation of the saccharified solution to the mixture.

5. The process for producing a saccharified solution according to claim 1, wherein the filtration is carried out using, as the filtration unit, a filter press having a structure consisting of a plurality of vertical filter plates arranged parallelly, a filter chamber formed between a pair of adjacent filter plates and filter cloths lined along an internal configuration of the filter chamber, by feeding the mixture into the filter chamber under applied pressure, allowing a cake composed of the undecomposed biomass residue to form on the filter cloths, then pressing the plurality of filter plates arranged parallelly in a direction in which one thereof overlaps another, and compressing a treated liquid in the filter chamber between the filter cloths.

6. The process for producing a saccharified solution according to claim 1, wherein the biomass is lignocellulosic biomass.

7. The process for producing a saccharified solution according to claim 1, wherein the mixture has a particle size distribution of two peaks, and particles in one of the two peaks having an average particle size of 0.2 μm are flocculated with each other and coarsened, and then removed.

* * * * *